US006800855B1

(12) United States Patent
Dong et al.

(10) Patent No.: US 6,800,855 B1
(45) Date of Patent: Oct. 5, 2004

(54) SPECTROSCOPIC METHOD FOR ANALYZING ISOTOPES BY USING A SEMICONDUCTOR LASER

(75) Inventors: Jie Dong, Tokyo (JP); Katsumasa Suzuki, Tokyo (JP); Hiroshi Masusaki, Tokyo (JP); Koh Matsumoto, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/472,585

(22) Filed: Dec. 27, 1999

(51) Int. Cl.[7] .................................................. G01J 5/02
(52) U.S. Cl. ................................................. 250/339.13
(58) Field of Search ....................... 250/339.12, 339.13, 250/339.06, 339.07, 343, 345

(56) References Cited

U.S. PATENT DOCUMENTS

| 4,990,780 A | * | 2/1991 | Lee et al. ..................... 250/343 |
| 5,394,236 A | * | 2/1995 | Murnick ....................... 356/311 |
| 5,464,980 A | * | 11/1995 | Spring et al. ................ 250/345 |
| 5,640,014 A | * | 6/1997 | Sauke et al. ............ 250/339.03 |
| 5,929,442 A | * | 7/1999 | Higashi .................. 250/339.13 |
| 6,028,310 A | * | 2/2000 | Atkinson ................ 250/339.13 |

FOREIGN PATENT DOCUMENTS

JP          10-281988          10/1998

OTHER PUBLICATIONS

J.H. Park, et al.; "Atlas of Absorption Lines From 0 to 17900 $cm^{-1}$"; *NASA Reference Publication 118*, 81987; pp. 1–2.

* cited by examiner

*Primary Examiner*—Georgia Epps
*Assistant Examiner*—Alicia M. Harrington
(74) *Attorney, Agent, or Firm*—Merchant & Gould P.C.

(57) ABSTRACT

The present invention provides a spectroscopic method for analyzing isotopes which makes it possible to simplify a system for measurement and to identify isotopes with high accuracy and sensitivity and to carry out quantitative analysis. The spectroscopic method for analyzing isotopes uses a semiconductor laser beam having as a wavelength zone a 2000 nm-wavelength band as a beam source of wavelengths of the absorption spectra of the isotopes. A reference gas is used for identification of the isotopes where the gas contains collating components having two wavelengths (W1, W2) of well-known absorption spectra in wavelength bands close to the wavelengths (w1, w2) of the absorption spectra of the isotopes.

5 Claims, 4 Drawing Sheets

Absorption spectra having 2000 nm wavelength band. Cited from "High Resolution Transmission Molecular Absorption

SPECTROSCOPIC METHOD FOR ANALYZING ISOTOPES BY USING A SEMICONDUCTOR LASER

BACKGROUND OF THE INVENTION

This invention relates to a method for identifying isotopes in gas to be measured(hereinafter, referred to as "sample gas") or for analysing abundance ratio and concentration thereof with high accuracy and sensitivity from absorption spectra of sample gas on which the spectra are measured by using a semiconductor laser beam.

In a medical field, diagnosing and grasping conditions of sorts of organs of the body is carried out by giving stable isotopes to the body and analysing isotopes contained in exhausted expiration. For example, a method for examining $^{13}$C-urea expiration has been recently used to diagnose whether the body is infected with Helicobacter pylori bacteria or not with relation between gastritis or gastric ulcer and gastric infection with Helicobacter pylori bacteria. This is a method for analysing conditions of patient's organs by measuring amount of $^{13}$CO$_2$ gas contained in patient's expiration after giving a $^{13}$CO-marked compound to the patient who suffers gastritis or gastric ulcer.

For this, the method for examining $^{13}$C-urea expiration requires means for analysing stable isotopes appropriately. A mass spectroscopy and a method for an infrared spectroscopic analysis using an infrared lamp or the like are known as methods for analysing the isotopes.

However, the mass spectroscopy has problems of complexity in operating the apparatus and high cost of the apparatus, while analysing isotopes with high accuracy. Thus, the method for an infrared spectroscopic analysis has been generally adopted which uses a small difference between absorption wavelengths in relation with infrared rays of $^{13}$C/$^{12}$C, caused by the difference between mass of isotopes $^{13}$C/$^{12}$C. A spectroscopic analyser using an infrared lamp used in a method for an infrared spectroscopic analysis has many uses because of its convenience and low cost but has low accuracy so that a spectroscopic method for analysing isotopes by using a semiconductor laser which oscillates a beam having a 1570 nm(10$^{-9}$ m)-band wavelength has been recently suggested.

But, this wavelength of 1570 nm(10$^{-9}$ m)-band zone has a small absorption coefficient of carbon dioxide gas(CO$_2$) so that a high sensitive analysis is hardly achieved. Thus, a preparatory process such as a concentrating process using an absorbent absorbing CO$_2$ gas contained in expiration at a lower temperature has been performed in order to increase sensitivity. Moreover, the wavelength band is the zone in which various kinds of molecules are absorbed and in which there exist a plurality of adjacent absorption line peaks of isotopes so that it is difficult to specify absorption lines of isotopes $^{13}$C/$^{12}$C to be measured. Because of that, the isotopes $^{13}$C/$^{12}$C are identified through measuring by using various kinds of gases that the respective concentrations of the isotopes $^{13}$C/$^{12}$C are varied.

SUMMARY OF THE INVENTION

A spectroscopic method for analysing isotopes by using a semiconductor laser having a wavelength zone of 2000 nm(1990~2060 nm) band has been recently under development. In this wavelength zone, an absorption intensities of isotopes $^{13}$C/$^{12}$C are greater than those of 1570 nm-band zone by two digits and sensitivities thereof are accordingly greater by about two digits. And it is appreciated that the new method has an advantage that a preparatory process concentrating isotopes which is required in the spectroscopic analysis of 1570 nm-band zone in order to increase a sensitivity is not required. Therefore, in a spectroscopic method for analysing isotopes, the inventors of the present invention aimed at using a semiconductor laser beam having a 2000 nm-band zone based on the aforementioned advantage and it is an object of the present invention to provide a spectroscopic method for analysing isotopes in order to identify isotopes and carry out quantitative analysis with high accuracy and sensitivity with a simple system accurately distributing the semiconductor laser beam having 2000 nm-band zone.

In order to achieve the above mentioned object, the first aspect according to the present invention provides a spectroscopic method for analysing isotopes contained in gas to be measured by identifying and quantitatively measuring isotopes by using wavelengths of absorption spectra absorbed in existence of said isotopes, the improvement is characterized in that the method comprises the steps of using a semiconductor laser beam as a beam source for said wavelengths of said absorption spectra; and using a reference gas for identification of said isotopes, wherein said reference gas contains collating components having two wavelengths of well-known absorption spectra in wavelength band close to said wavelengths of absorption spectra of said isotopes.

Furthermore, the second aspect according to the present invention provides the spectroscopic method for analysing isotopes according to the first aspect, wherein said collating components contained in said reference gas is hydrogen bromide; and said collating components of said two wavelengths of said well-known reference absorption spectra are H$^{79}$Br and H$^{81}$Br.

Furthermore, the third aspect according to the present invention provides the spectroscopic method for analysing isotopes according to the first or the second aspect, wherein said isotopes to be measured are isotopes of carbon dioxide gas.

Furthermore, the fourth aspect according to the present invention provides the spectroscopic method for analysing isotopes as in any of the preceeding aspects, wherein said semiconductor laser beam source emits spectra having wavelength zone of 2000 nm band.

Furthermore, the fifth aspect according to the present invention provides the spectroscopic method for analyzing isotopes according to the third or the fourth aspect, wherein said said isotopes of carbon dioxide gas as sample gas are $^{12}$CO$_2$ and $^{13}$CO$_2$ and said $^{12}$CO$_2$ and $^{13}$CO$_2$have pairs of the following wavelengths (a wavelength of isotope $^{12}$C$_2$(nm)):(a wavelength of isotope $^{13}$CO$_2$(nm))

2054.37:2053.96
2044:2044.49
2035.34:2035.63
2010.18:2010.29
2002.51:2002.54
1995.99:1996.10 and a abundance ratio is measured by an absorbance in accordance with said a respective pair of wavelengths.

Furthermore, the sixth aspect according to the present invention provides the spectroscopic method for analysing isotopes by using a semiconductor, is which comprises the steps of identifying said isotopes by using absorption spectra of hydrogen bromide as reference gas having well-known collating components, said absorption spectra having wavelength band according to the fourth aspect; and identifying existence of impurities generating absorption spectra at said wavelength band.

DESCRIPTION OF THE PREFERRED EMBODIMENTS

Figure 1:
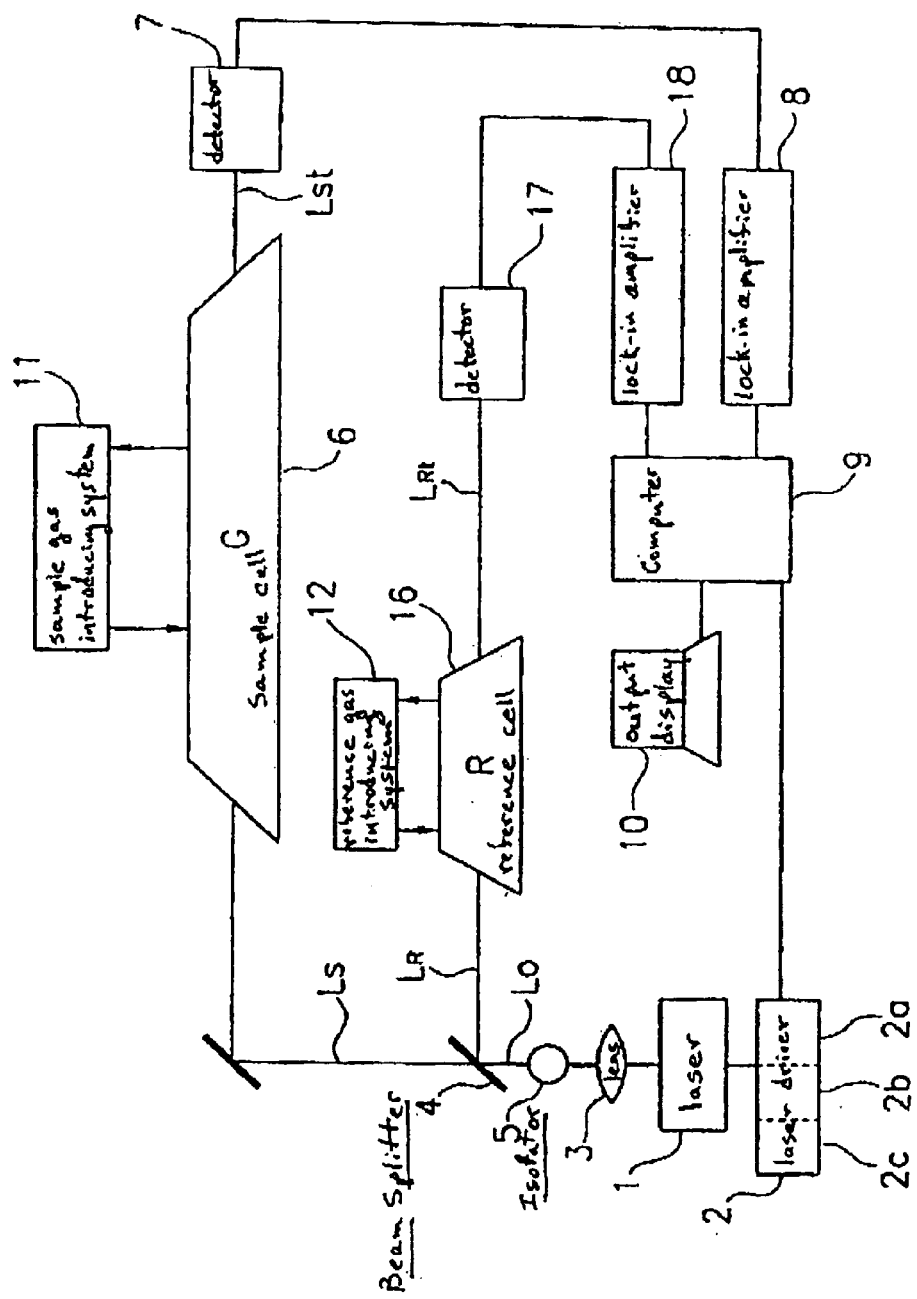
FIG. 1 is a schematic diagram of system showing an embodiment of a spectroscopic analysis apparatus using a semiconductor laser.

A preferred embodiment of the present invention will be described hereinafter. A spectroscopic method for analyzing isotopes according to the present invention is carried out by a spectroscopic analysis apparatus using a semiconductor laser shown in FIG. 1. That is to say, FIG. 1 is a schematic diagram of a system showing an embodiment of a spectroscopic analysis apparatus using a semiconductor laser according to the present invention. A semiconductor laser beam source 1 oscillating a laser beam having 2000 nm-wavelength band is driven by a laser driver 2. For oscillating a desired and appropriate laser beam, the laser driver 2 comprises a temperature controller 2a for controlling appropriately a temperature of a laser element, a laser diode (hereinafter, referred to as "LD") driver 2b for providing the laser element with an electric current and driving the same, and a function generator 2c as a frequency modulating means for modulating oscillating frequency of the laser based on frequency modulation. Moreover, these 2a,2b,2c are coupled to a computer 9 for an appropriate operation.

Moreover, in the laser driver 2, an operating temperature of the laser element is controlled and oscillating wavelengths are continuously varied by varying continuously an injection current(direct current) into the laser element and modulated signals(a alternating current component) based on frequency modulation are introduced into the LD driver 2b by the function generator 2c and frequency modulation is directly applied to the laser beam oscillated from the laser element by overlapping the modulated signals with the injection current into the laser element.

As the semiconductor laser beam source 1 radiating spectra having a wavelength zone of 2000 nm(1990~2060 nm), which is thus oscillated by the driver 2, a semiconductor distributed feedback laser(DFB laser) of infrared InGaAs/InGaAsP can be preferably used.

Also, The semiconductor laser having 2000 nm-band zone is arranged to obtain a laser oscillation up to a wavelength of 2100 nm by introducing highly compressed and distorted quantum well into an activated layer of a laser.

Thus, a laser beam $L_O$ of the oscillating semiconductor laser beam source 1 is condensed in a condenser lens 3 and thereafter, divided into two beams $L_S$, $L_R$ in a beam splitter 4. Also, for preventing constant transmission of a laser beam from being dispersed due to re-injection of reflected rays from the beam splitter 4 into an optical path, it is preferable to provide an isolator 5(a reflected rays remover)in the optical path which is positioned after condensation in the condenser lens 3 and before a incidence into the beam splitter 4. Moreover, the beam Ls of one side is transmitted into a sample cell 6 where sample gas G containing isotopes to be measured is supplied and then, the transmitted beam $L_{St}$ coming through the sample cell 6 is received by a beam detector 7 and photoelectrically converted by a sensor such as an InGaAs photo diode or the like and output signals thereof are introduced into a lock-in amplifier 8. In the lock-in amplifier 8, only a second order differential signals are output by processing the signals from the beam detector 7 and the output signals thereof are introduced into the computer 9. A reference number 10 represents a displayer displaying data accumulated in the computer.

Moreover, the computer 9 stores and accumulates the data for oscillating semiconductor laser beam appropriately at all times and transmits a control or an operation signal to the laser driver 2 according to an appropriate operational condition and makes the semiconductor laser beam source 1 emit a beam properly at all time.

Also, a beam $L_R$ of another side divided from the beam splitter 4 is transmitted into a reference cell 16 to which reference gas G containing mixture components having well-known wavelengths of absorption spectra. And the transmitted beam coming through the reference cell 16 is received in a beam detector 17 and photoelectrically converted by a sensor such as an InGaAs photo diode or the like, and the output signals thereof are introduced into a lock-in amplifier 18. The lock-in amplifier 18 processes the signals from the beam amplifier 18 and outputs only second order differential signals, and the signals are introduced into the computer 9.

Moreover, the magnitude of the second order differential signals derived from the lock-in amplifier 8,18 depends on absorbance of a laser beam by the sample gas G or the reference gas R and the greater concentrations of beam absorption components are in the gas, the smaller the signals are. Also, the laser beam is absorbed when it is identical with absorption wavelengths of isotopes and the detected beam signals by the beam detector 7,17, the beam signals of the transmitted beam $L_{St}$, $L_{Rt}$ coming through the sample cell 6 or the reference cell 16 become smaller.

Thus, the spectra of the transmitted beam $L_{St}$ coming through the sample cell 6 to which the sample gas G is introduced, is detected by the beam detector 7 and photoelectrically converted. The output thereof is processed in the lock-in amplifier 8 and only second order differential signals are selectively output, and the signals are introduced into the computer 9.

In the same manner, at the same time, the spectra of the transmitted beam $L_{Rt}$ coming through the sample cell 16 to which the reference gas having well-known wavelengths of absorption spectra is introduced, are detected by the beam detector 17 and photoelectrically converted. The output thereof is processed in the lock-in amplifier 18 and only second order differential signals are selectively output, and the signals are introduced into the computer 9.

And in the computer 9: the absorption spectra of the transmitted beam $L_{St}$ coming through the sample cell 6 to which the sample gas G is introduced, are collated and compared with the well-known absorption spectra of the transmitted beam coming through the cell 16 to which the reference gas R having well-known absorption spectra is introduced and the isotopes to be measured contained in the sample gas G are identified by the wavelengths shown up in the absorption spectra and at the same time compared with the values of the magnitude of the well-known absorption spectra in order to compute and produce the abundance ratios and concentrations of the isotopes contained in the sample gas G.

Furthermore, reference number 11 represent a sample gas introducing system which is connectively arranged to the sample cell 6 and which system container. Also, reference number 12 represents a reference gas introducing system which is connectively arranged to the reference cell 16 and which system consists of an air pump exhausting inside of the cell 16 and a reference gas storing container.

And the present invention is characterized by using the gas, as the reference gas R having well-known absorption spectra, which is introduced into and used in the reference cell 16 and the gas fulfills the following conditions or the like:

①The gas is the one where there exist absorption spectra thereof at adjacent wavelength intervals of several nanometer.

② The gas is the one where absorption intensities of absorption spectra of isotopes where there exist spectra adjacently are almost same ones.

Figure 2:
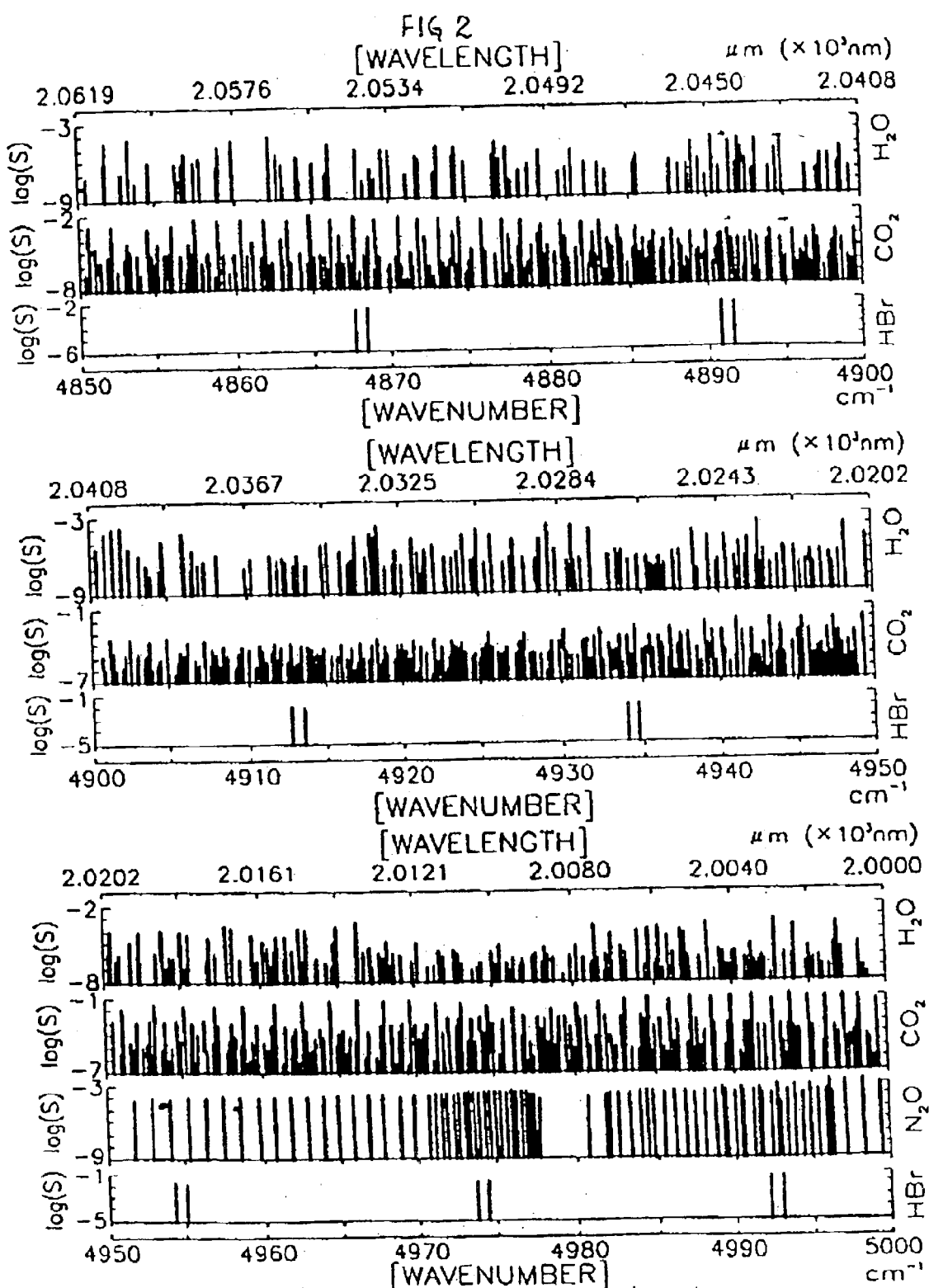
FIG. 2 is an absorption spectra diagram showing an examples of absorption spectra having 2000 nm-wavelength band.

A concrete example of the gas is hydrogen bromide as shown in FIG. 2, an absorption spectra diagram showing an example of absorption spectra having a 2000 nm-band wavelength, and Hydrogen bromide is known that there exist two strong wavelengths of absorption spectra at 0.3 nm interval in the wavelength band of 1930~2100 nm as the wavelengths of absorption spectra of isotopes $H^{79}Br/H^{81}Br$ and absorption intensities are almost same, so that it can be preferably used as the reference gas R according to the present invention.

Moreover, as the reference gas R of the present invention besides the hydrogen bromide, isotopes $^1H_2O/^2H_2O$ of water ($H_2O$) and isotopes $^{14}N_2O/^{15}N_2O$ of nitrogen oxide($N_2O$) may be used as well.

Also, the FIG. 2 was cited from "High Resolution Transmission Molecular Absorption Data Base" issued by Air Force Geophysics Laboratory of U.S.A. in 1986.

Moreover, the schematic diagram of system in FIG. 1 illustrates such an example where the reference gas R is introduced into the reference cell 16 and the sample gas is introduced into the sample cell 6 which is arranged parallel with the reference cell 16 and the transmitted beams $L_{St}$, $L_{Rt}$ coming through the cells 16,6 are detected and then the identification or computation of abundance ratio is performed by comparing and computing the detected values in the computer 9. However, the reference cell 16 is not always required and only the sample cell 6 may be provided. In this case, the reference gas R is introduced into the sample cell 6 before the sample gas G is introduced into to the sample cell 6 for measurement. Then, the absorption spectra of the reference gas are obtained through the measurement, which are stored in the computer 9. Subsequently, the sample gas G is introduced into the sample cell 6 in order to obtain the absorption spectra of the sample gas, which are introduced into the computer 9 in order to be collated and compared with the absorption spectra of the previously stored reference gas R, whereby to obtain the analyzed result.

Hereinafter, a method for identifying isotopes and for analysing and measuring concentrations of isotopes and abundance ratios of those using the aforementioned spectroscopic analysis apparatus in the computer 9 will be described. The sequence of an operation is as follows:

(1) The absorption spectra of the reference gas G are measured.

Corresponding the relation between driving currents [Y1, Y2](mA) and wavelengths [W1, W2](nm) of the absorption spectra of the reference gas R is obtained by the same laser diode(LD).

(2) The position relation between the wavelengths of the absorption spectra of the isotopes of the sample gas G and the isotopes is specified.

① The relation between the absorption spectra and the isotopes is specified by varying the content of isotope of one side and examining the accordingly changed state of the absorption spectra.

②The corresponding relation of the driving currents [y1, y2](mA) of the absorption spectra of the sample gas G is obtained by the same laser diode(LD).

(3) the wavelengths of the absorption spectra of the isotopes of the sample gas G are computed and decided.

① From the relation obtained from the term (1), which is the relation between the wavelengths of the absorption spectra of the well-known isotopes of the reference gas R and the driving currents[Y1 ,Y2] of the wavelengths [W1, W2](nm) of the spectra by the same laser diode(LD), the rate of change [Z](nm/mA) of the wavelengths [W1, W2](nm) of the absorption spectra of well-known isotopes to the driving currents [Y1, Y2](mA) of the semiconductor laser is obtained by the following equation:

$$Z=(W2\cdot W1)/(Y2\cdot Y1) \quad (1)$$

② Subsequently, by using the driving current values [y1, y2](mA) of the laser diode(LD) emitting the wavelengths of the absorption spectra, the relation between the wavelengths [W1, W2] of the well-known absorption spectra of the reference gas R and the driving currents [y1, y2](mA) thereof and the rate of change [Z] thereof, the wavelengths [w1, w2](nm) of the absorption spectra of the isotopes of the sample gas G of the term (2) is computed and decided by the following equation:

$$w2=(y2\cdot Y2)\times Z+W2 \quad (2)$$

$$w2=(y1\cdot Y1)\times Z+W1 \quad (3)$$

(herein, w2>w1, W2>W1)

Moreover, since wavelengths are varied due to the temperature fluctuation of the semiconductor laser beam source 1, a correction of a temperature needs to be performed in the above equation. But when a temperature is appropriately controlled by the laser driver 2 like the semiconductor laser beam source 1 according to the present invention, it is possible to compute and decide the wavelengths of the isotopes in the above equation within an error range of 0.5 nm and less without a correction of a temperature.

(4) The abundance ratios and concentrations of isotopes of the sample gas G are computed.

Thus, the wavelengths of the absorption spectra of the isotopes of the sample gas G are precisely identified. And the abundance ratios of the isotopes are obtained by outputting the absorbance ratios through measuring the absorbance ratios in accordance with the absorption spectra of the identified isotopes. Furthermore, concentrations of the isotopes contained in the sample gas G are precisely output by the application of the absorption coefficient of the isotopes in accordance with intensities of the absorption spectra and the spectra of the wavelengths.

Moreover, practically, it becomes very easy to measure concentrations when a scale-marked calibration curve is made by measuring the relation between concentrations of isotopes to be measured and absorption intensities of wavelengths of absorption spectra with a well-known concentration and the curve is stored in the computer 9.

Now, the embodiment according to the present invention is described. In the embodiment hereinafter, a distributed feedback laser(DFB laser) having 2000 nm-wavelength band(1990~2060 nm) is used as the semiconductor laser source 1 and the wavelengths thereof are varied at 0.02 nm/mA.

Since a width of an emitted beam of the laser is narrowed and sharpened up to about 10 MHz(0.1 cm$^{-1}$) by using the DFB laser, which width is about 1/50 of the width of absorbed beam of isotopes $^{12}CO_2/^{13}CO_2$ for example, it is possible to analyze precisely absorption spectra of isotopes.

[The First Embodiment of the Present Invention]

Isotopes $^{12}CO_2/^{13}CO_2$ contained in carbon dioxide gas as the sample gas were identified by the method according to the present invention.

① The absorption spectra were measured by using Hydrogen bromide(HBr) as the reference gas R.

As shown in FIG. 2, hydrogen bromide where there exist two simple absorption spectra at several nm intervals has been generally known about the wavelengths thereof and has been used effectively. Then, the driving currents(Y1, Y2) of the laser diode(LD) in the semiconductor laser used in the present invention, where the currents correspond to the wavelengths(W1, W2) of the absorption spectra of the isotopes H$^{79}$Br/HB$^{81}$Br of a well-known hydrogen bromide, were measured by maintaining the temperature of the laser at 25° C. these are shown in chart 1.

CHART 1

| LD No | wavelengths of H$^{81}$Br [W2] (nm) | driving current for oscillation [Y2] (mA) | wavelengths of H$^{79}$Br [W1] (nm) | driving current for oscillation [Y1] (mA) | the rate of change Z = (W2·W1)/ (Y2·Y1) |
|---|---|---|---|---|---|
| LD1 | 2054.31 | 65.5 | 2054.02 | 51.8 | 0.0211 |
| LD2 | 2044.68 | 73.2 | 2044.27 | 50.1 | 0.0177 |
| LD3 | 2035.49 | 61.0 | 2035.23 | 48.3 | 0.0205 |
| LD4 | 2010.55 | 57.6 | 2010.26 | 43.5 | 0.0206 |
| LD5 | 2003.09 | 68.4 | 2002.80 | 53.9 | 0.0200 |
| LD6 | 1996.04 | 76.1 | 1995.75 | 60.8 | 0.0190 |

② Subsequently, the absorption spectra of the isotopes $^{12}CO_2/^{13}CO_2$ of the sample gas were obtained and the corresponding relation between the absorption spectra and the isotopes $^{12}CO_2/^{13}CO_2$ was identified.

First, the absorption spectra of the nitrogen gas containing 10% of carbon dioxide gas having a concentration ratio (99:1) of the isotopes $^{12}CO_2/^{13}CO_2$ were obtained. As a result, a spectra line graph having three absorption peaks a, b, c which are designated to reference sign X in FIG. 3 was obtained.

Subsequently, the small amount of isotope $^{13}CO_2$ were added to the gas in order to increase the mass thereof and then, the absorption spectra of the gas having the increased concentration of the isotope $^{13}CO_2$ were obtained. As a result, a spectra ling graph having four absorption peaks o, p, q, r which are designated to reference sign Y in FIG. 3 was obtained.

Figure 3:
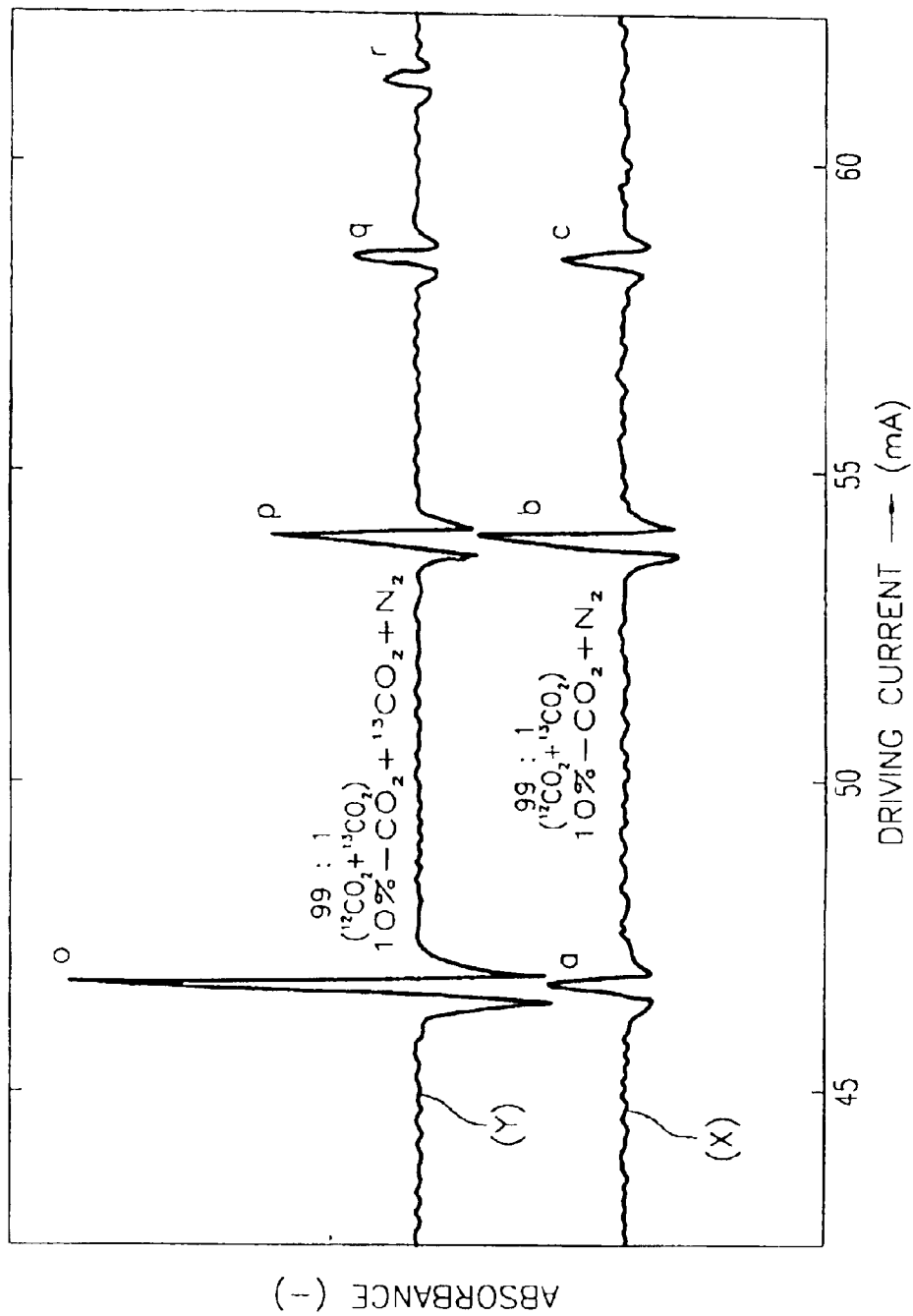
FIG. 3 is an absorption spectra diagram showing a fluctuation of absorption spectra of isotopes of carbon dioxide gas whose concentrations of isotopes are varied.

Here, when comparing the absorption spectra line graphs of X, Y of FIG. 3, each peak was shown up in the same position(the same value of driving currents) in accordance with a-o, b-p, c-q, -r except the peak r. And in the absorption spectra line graph Y of the gas having an increased concentration of the isotope $^{13}CO_2$, the peak o corresponding to the peak a of the absorption spectra line graph X became higher. Moreover, the peak which was not shown in the absorption spectra line graph X of the gas, was shown up as peak r in the absorption spectra line graph Y of the gas having an increased concentration of the isotope $^{13}CO_2$. As a result of this, the fact that the peaks a-o, r were the absorption spectra of the isotope $^{13}CO_2$ and the peaks b-p, c-q were the absorption spectra of the isotope $^{12}CO_2$ was identified and decided.

Without limiting to the isotopes of carbon dioxide gas, when identifying and deciding what kinds of isotopes are these, it is possible in the same manner to decide by obtaining an respective absorption spectra line graph through varying concentration ratios of isotopes and by examining the change thereof.

③ Subsequently, the absorption spectra of the isotopes $^{12}CO_2/^{13}CO_2$ of the sample gas were obtained and the driving current values(y1, y2) of the laser diode(LD) emitting the wavelengths of the absorption spectra were measured. Moreover, the fact that the wavelengths oscillating with the driving current value y2 were those of the isotope $^{12}CO_2$ was identified by the work specifying the correspondence with the isotopes of absorption wavelengths of the ②, this is shown in chart 2.

CHART 2

| LD No | driving current for oscillation [y2] (mA) | wavelengths of $^{12}CO_2$ [w2] (nm) | driving current for oscillation [y1] (mA) | wavelengths of $^{13}CO_2$ [w1] (nm) |
|---|---|---|---|---|
| LD1 | 68.3 | 2054.37 | 49.0 | 2053.96 |
| LD2 | 71.5 | 2044.65 | 62.5 | 2044.49 |
| LD3 | 53.7 | 2035.34 | 67.8 | 2035.63 |
| LD4 | 36.9 | 2010.18 | 45.0 | 2010.29 |
| LD5 | 39.4 | 2002.51 | 40.9 | 2002.54 |
| LD6 | 73.5 | 1995.99 | 79.3 | 1996.10 |

④ the wavelengths of the absorption spectra of the isotopes $^{12}CO_2/^{13}CO_2$ of the sample gas, which were obtained in the work of the item ③ were obtained.

The wavelengths(w1, w2) of the absorption spectra of the isotopes $^{12}CO_2/^{13}CO_2$ of the sample gas was decided by applying the followings to the equation (2),(3): the LD driving current values(y1, y2) of the wavelengths of the absorption spectra of the isotopes $^{12}CO_2/^{13}CO_2$ of the sample gas, which were obtained from the item (③) and the driving current values(Y1, Y2) of the semiconductor laser diode(LD) used in the present embodiment, which corresponded to the wavelengths(W1, W2) of the absorption spectra of the isotopes H$^{79}$Br/H$^{81}$Br of a well-known hydrogen bromide as the reference gas R, which values were obtained from the item ① and the rate of change Z [Z=(W2·W1)/(Y2·Y1)] thereof.

Figure 4:
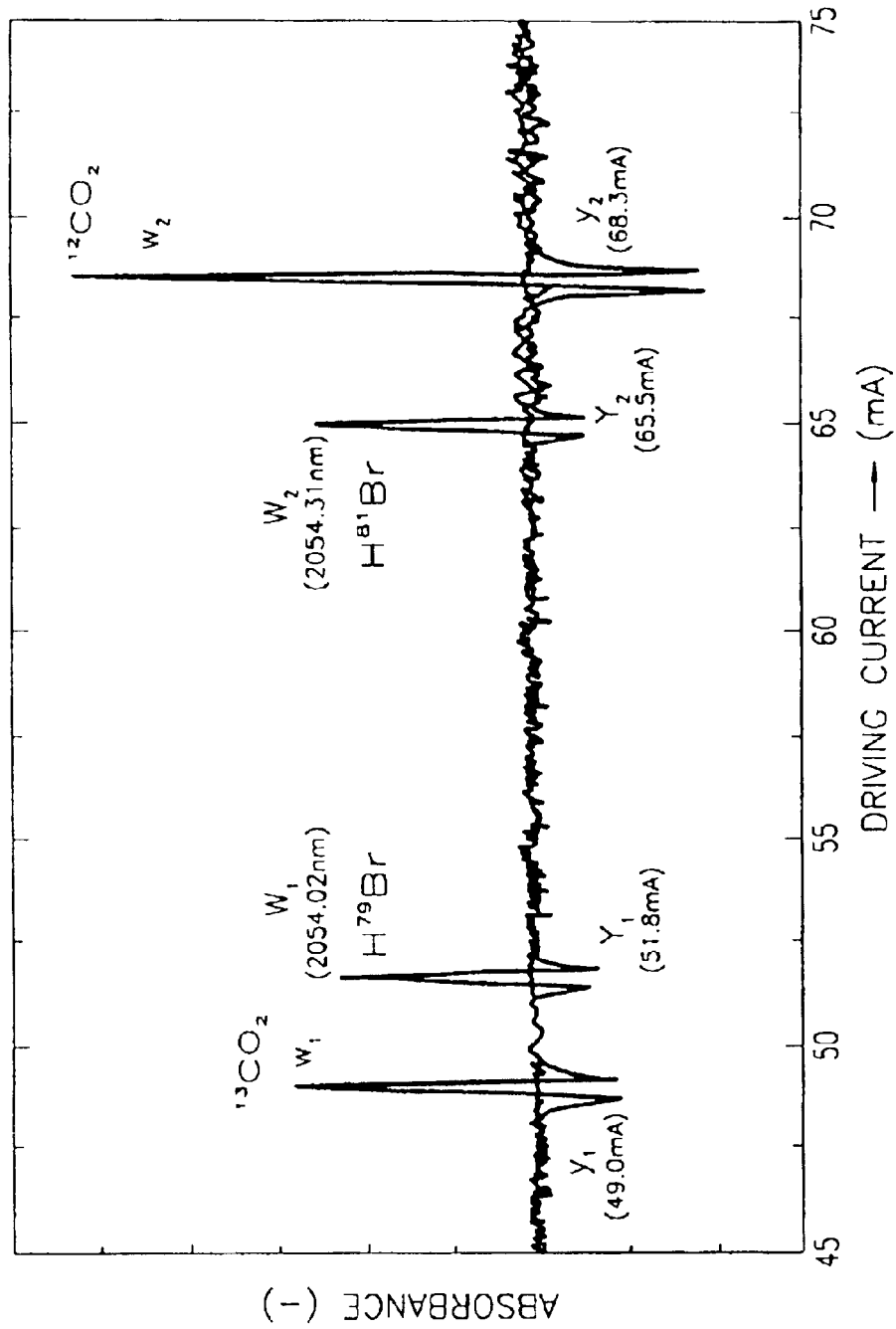
FIG. 4 is an absorption spectra diagram showing of a spectroscopic method for analysing isotopes of carbon dioxide gas contained in sample gas by using HBr as reference gas according to the present invention.

FIG. 4 is a spectra diagram of absorption spectra of isotopes $^{12}CO_2/^{13}CO_2$ contained in carbon dioxide gas as the sample gas G, which were measured by using hydrogen bromide as reference gas R and using the apparatus shown in FIG. 1, which apparatus used the laser beam emitted from the laser diode LD1. The wavelengths(w1, w2) of the absorption spectra of the isotopes $^{12}CO_2/^{13}CO_2$ of the sample gas was decided by this absorption spectra graph.

When the laser diode LD1 was used, the wavelength [w2] of the absorption spectra of the isotope $^{12}CO_2$ can be obtained by the equation (2), w2=(y2·Y2)×Z+W2. Therefore, when the values of chart 1, chart 2 were substituted to the equation (2), the result became as follows:

$$w2 = (68.3 \cdot 65.5) \times 0.0211 + 2054.31 = 2.8 \times 0.0211 + 2054.31 = 2054.37$$
(nm)

Also, the wavelength [w1] of the absorption spectra of the isotope $^{12}CO_2$ can be obtained by the equation (3), w1=(y1·Y1)×Z+W1. Therefore, when the values of chart 1, chart 2 were substituted to the equation (3), the result became as follows:

w=(49.0·51.8)×0.0211+2054.02=2.8×0.0211+2054.02 =0.0591 +2054.02=2053.96 (nm)

the Wavelengths of the absorption spectra of the isotopes were decided in the same manner by using the driving current values of the absorption wavelengths of the isotopes of the sample gas shown in FIG. 2 in accordance with the laser diode LD2, 3, . . . n, these are shown in FIG. 2.

⑤ From the absorption intensities of the absorption spectra of the isotopes $^{12}CO_2/^{13}CO_2$ of the sample gas, which were thus obtained, the abundance ratios and the concentrations of these isotopes were obtained.

Since the absorption intensities of the absorption spectra of the isotopes $^{12}CO_2/^{13}CO_2$ obtained from the item ④ as shown in chart 2 were proportional to the concentrations, the abundance ratios of the isotopes $^{12}CO_2/^{13}CO_2$ can be obtained by measuring the absorption intensities of the absorption spectra and computing the both ratios.

Moreover, the absolute values of concentrations associated with the absorption intensities of the absorption spectra can be obtained by inserting absorption coefficients in the relevant wavelengths of the isotopes $^{12}CO_2/^{13}CO_2$.

Moreover, since absorption spectra of impurities are shown up as well when there exist impurities, it is possible not only to remove effects of the impurities but also to analyse that impurities in the same manner.

Practically, it becomes very easy to measure concentrations when a scale-marked calibration curve is made by measuring the relation between concentrations of isotopes to be measured and absorption intensities of wavelengths of absorption spectra with a well-known concentration and the curve is stored in the computer 9.

The aforementioned embodiment was disclosed with carbon dioxide gas as example isotopes of a sample gas. But the present invention is not limited to this and it is needless to say that the present invention is effectively applicable to any isotope especially where there exist absorption spectra having 2000 nm-wavelength band. And in accordance with the present invention, it is possible to analyse isotopes with high accuracy and a sensitivity.

The present invention can be carried out as the above mentioned embodiment and has effects described hereinafter.

As the present invention uses a reference gas such as hydrogen bromide where the wavelengths of the absorption spectra are shown up at several nm intervals and the gas which has two well-known adjacent spectra lines whose absorption intensities are almost same, the present invention is very simply and effectively utilized for identifying absorption spectra of isotopes.

Furthermore, it becomes easy to identify wavelengths of absorption spectra of isotopes of a sample gas by using the above mentioned gas as a reference gas for identifying isotopes and it is also possible to output very easily absolute values of concentrations with high accuracy.

Furthermore, it is possible to detect impurities other than isotopes which are objects to be measured in a sample gas. Especially when positions of wavelengths of absorption spectra of impurities are already known, it is also possible to specify the impurities.

Furthermore, since the wavelength band of the semiconductor laser beam used in the present invention is 2000 nm and absorption of impurities is relatively smaller than a conventional laser beam having 1570 nm band, it is possible to obtain favorable absorption spectra which have few effects according to absorption due to existence of impurities (overlapping of absorption spectra etc). The present invention has prominent and unique effects aforementioned.

What is claimed is:

1. A spectroscopic method for analysing isotopes contained in gas to be measured by identifying and quantitatively measuring isotopes by using wavelengths of absorption spectra absorbed in existence of said isotopes, the improvement is characterized in that the method comprises the steps of using a semiconductor laser beam as a beam source for said wavelengths of said absorption spectra; and using a reference gas selected from the group consisting of hydrogen bromide, water, nitrogen oxide and mixtures thereof for identification of said isotopes, wherein said reference gas.

2. The spectroscopic method for analysing isotopes according to claim 1, wherein said semiconductor laser beam source emits a beam of spectra having wavelength zone of 2000 nm band.

3. The spectroscopic method for analyzing isotopes according to claim 2, wherein said isotopes of carbon dioxide gas as sample gas are $^{12}CO_2$ and $^{13}CO_2$; and said $^{12}CO_2$ and $^{13}CO_2$ have pairs of following wavelengths (a wavelength of isotope $^{12}CO_2$(nm)):(a wavelength of isotope $^{13}CO_2$(nm))

2054.37:2053.96
2044:2044.49
2035.34:2035.63
2010.18:2016.29
2002.51:2002.54
1995.99:1996.10 and a abundance ratio is measured by an absorbance in accordance with said a respective pair of wavelengths.

4. The spectroscopic method for analysing isotopes by using a semiconductor, which comprises the steps of identifying said isotopes by using absorption spectra of hydrogen bromide as reference gas having well-known collating components, said absorption spectra having wavelength band according to claim 4; and identifying existence of impurities generating absorption spectra at said wavelength band.

5. The spectroscopic method for analyzing isotopes according to claim 1, wherein said isotopes of carbon dioxide gas as sample gas are $^{12}CO_2$ and $^{13}CO_2$; and said $^{12}CO_2$ and $^{13}CO_2$ have pairs of following wavelengths (a wavelength of isotope $^{12}CO_2$(nm)):(a wavelength of isotope $^{13}CO_2$(nm))

2054.37:2053.96
2044:2044.49
2035.34:2035.63
2010.18:2010.29
2002.51:2002.54
1995.99:1996.10 and a abundance ratio is measured by an absorbance in accordance with said a respective pair of wavelengths.

* * * * *